Figure 1:
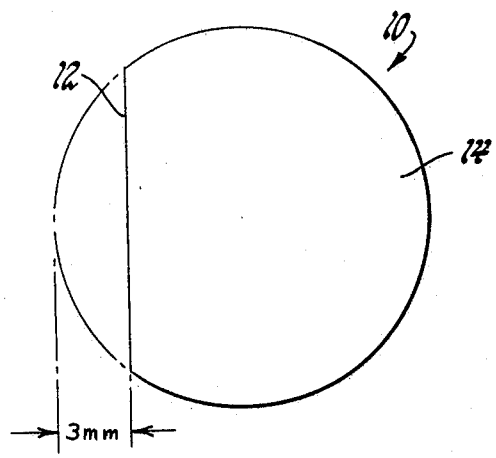

United States Patent [19]

Miller

[11] 4,346,996
[45] Aug. 31, 1982

[54] STANDARD REFLECTIVE DEVICE

[75] Inventor: Carl E. Miller, Millington, Mich.

[73] Assignee: General Motors Corporation, Detroit, Mich.

[21] Appl. No.: 199,973

[22] Filed: Oct. 23, 1980

[51] Int. Cl.³ ............................................. G01N 21/55
[52] U.S. Cl. ................................. 356/243; 250/252.1; 356/445
[58] Field of Search ....................... 356/243, 445–448, 356/128; 250/252

[56] References Cited

U.S. PATENT DOCUMENTS 2,215,211  9/1940  Devol ................................... 356/448
4,047,032  9/1977  Judge et al. .......................... 356/446

Primary Examiner—Vincent P. McGraw
Attorney, Agent, or Firm—Warren D. Hill

[57] ABSTRACT

A reflecting standard for an optical apparatus comprises a semitransparent crystal or glass which reflects from its front surface a predetermined proportion of the incident light dependent upon the index of refraction at the wavelength of the incident light. The rear surface of the reflector is disposed at an angle to the front surface and is provided with an antireflecting coating to minimize reflection therefrom.

1 Claim, 3 Drawing Figures

STANDARD REFLECTIVE DEVICE

This invention relates to a radiation reflecting standard for an optical apparatus.

For the calibration of optical systems, it is often necessary to have a standard reflective element which has a known reflectivity at a given wavelength of radiation. Frequently it is necessary to use a large number of substantially identical reflective standards at different times and at different locations. Further it is sometimes important to have a standard having a reflectivity of much less than 50 percent. The reflectivity of a clean smooth metal surface varies considerably with the wavelength of radiation. In addition, visually undetectable surface films cause large changes in reflectance values. Silver and aluminum are of particular interest as standard reflecting surfaces because they maintain high uniform reflectance across the near infrared region. Glass metalized with such materials is uniform, smooth and reproducible, however, the degree of reflectance is greater than 90 percent and thus has limited application.

For a lower range of reflectivity, stainless steel and tin coated steel have been proposed. However, they are characterized by surface features that produce diffuse images and diffraction. These conditions cause the intensity of the reflected radiation to be very sensitive to position and to the past history of the metal surface. Because of the microstructure of any prepared metal surface, no two pieces of metal will have identical surface features and consequently it is almost impossible to obtain a large number of standards having the same reflectivity.

It is therefore a general object of this invention to provide a standard reflecting device having a reflectivity of about 50 percent or even much lower. It is a further object to provide such a reflecting device which is accurately reproducible in large quantities and which has constant reflectance values over long periods of time.

The invention is carried out by providing a semitransparent crystal or glass material having a flat polished reflecting surface wherein the reflectivity is determined by the chemical composition of the material and having a rear surface inclined at an angle to the front surface and treated with antireflectance coating to minimize interference of reflection from the back surface with that from the front surface.

Figure 2:
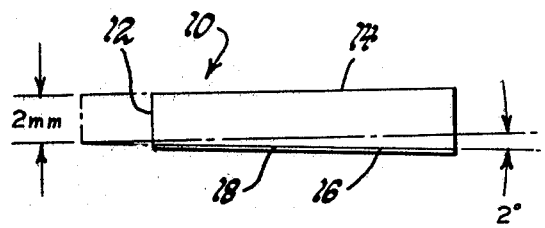
Figure 3:
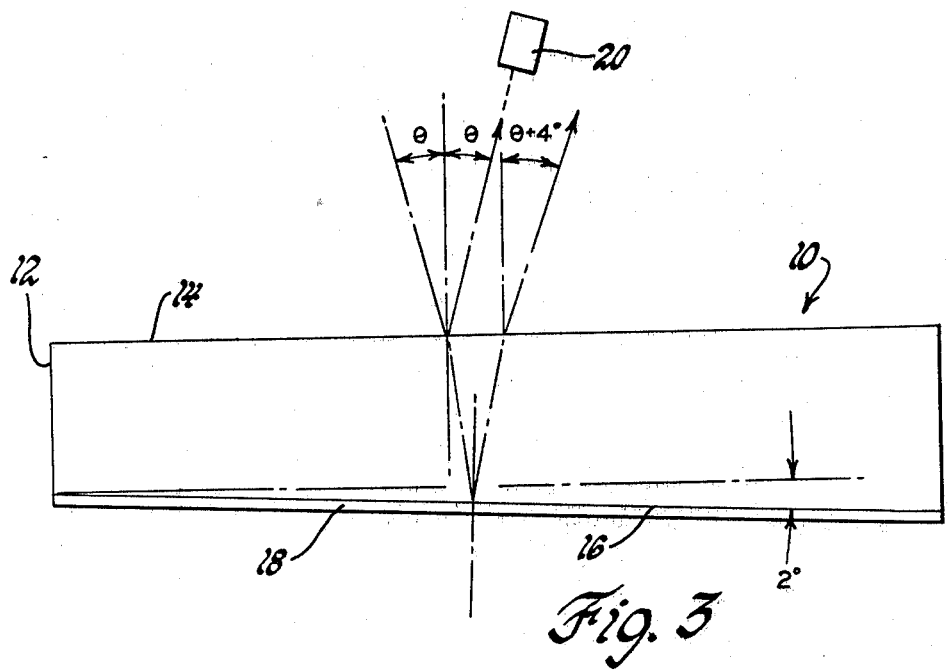

The above and other advantages will be made more apparent from the following specification taken in conjunction with the accompanying drawings wherein like reference numerals refer to like parts and wherein:

FIGS. 1 and 2 are top and side views respectively of a reflecting standard according to the invention, and FIG. 3 is a light ray diagram on an enlarged view of FIG. 2.

The reflecting standard is useful over a wide range of wavelengths. This description is particularly directed to a standard mirror for use in the near infrared range. It has been applied in a system using a wavelength of 940 nm. As shown in the drawings, a reflecting standard 10 is a substantially circular semitransparent solid wedge but with a flat 12 formed on one edge to serve as an orientation index. It has a front reflecting surface 14 which is smooth and flat and a rear surface 16 which is inclined at an angle of about two degrees with respect to the front surface 14. The rear surface 16 is coated with an antireflecting coating 18. The standard is, for example, about 25 millimeters in diameter and has a thickness on the order of 2 millimeters at its thinnest edge. The flat 12 is located at the thinnest edge. The front surface 14 is flat within 1,000 nm.

When radiation is incident on the front surface 14 and the specularly reflected portion is being monitored by a detector, it is advantageous to eliminate any ghost images reaching the detector caused by reflection of light from the rear surface 16. That is, the radiation transmitted through the front surface 14 and reaching the rear surface 16 should not be allowed to reflect from the rear surface back to the detector. The antireflecting coating 18 nearly eliminates such reflection. The antireflecting coating 18 is about 250 nm thick and preferably provides maximum extinction for 940 nm radiation incident from the front surface at an angle of 13 degrees. The maximum reflectance intensity from the coating in the range of 8 to 18 degrees should not exceed two or three percent. As shown in FIG. 3, the small amount of light which is reflected from the rear surface is reflected at such an angle that it diverges by 4 degrees from the path of the light reflected from the front surface and will not be incident on the detector 20 if the detector is judiciously located.

The material of the standard is a semitransparent crystal or a semitransparent glass. Such materials allow transmission of a portion of the incident light and reflection of the remainder from the surface 14. If at a given wavelength the index of refraction of the material is n, then the reflected portion R substantially equals $(n-1)^2/(n+1)^2$ for radiation incident at near normal angles (less than 45°). The following table lists several semitransparent substances suitable for a standard reflecting device and for each material gives the index of refraction n and the percent of radiation reflected R for a wavelength of 940 nm.

| Semitransparent Material | Index of Refraction (n) | Percent Reflected (R) |
| --- | --- | --- |
| Quartz | 1.5 | 4 |
| IR Glass | 1.75 | 7.4 |
| Silver Chloride | 2.01 | 11 |
| Zinc Sulfide | 2.28 | 15.2 |
| Arsenic Sulfide Glass | 2.4 | 16.9 |
| Silicon | 3.4 | 30 |
| Germanium | 4.1 | 37 |

These are but a few examples of the many semitransparent materials which are available. Thus by proper selection of the material, a reflectance standard can be provided having a reflected fraction well below 50 percent. These substances are chemically stable and since the reflected fraction depends upon the chemical composition, the reflectance of a given device does not vary with age. Moreover, it is easy to obtain a plurality of standards even from different sources and at different times having substantially identical reflecting properties.

To maintain consistent reflecting qualities, the standard device must be free from dust, fingerprints, etc. One method for cleaning the surface 14 is to gently wipe reagent grade chloroform on a cotton swab across the surface. Second, a collodion film formed on the surface and then peeled off will result in a clean mirror surface.

It is thus seen that an inexpensive accurately reproducible standard for light reflection is provided using inexpensive durable materials and allowing a selection of reflected fraction in a range well below 50 percent where previously a suitable standard has not been available.

The embodiments of the invention in which an exclusive property or privilege is claimed are defined as follows:

1. A standard reflecting device for an optical apparatus comprising a wedge shaped element having a flat polished front surface for specular reflection of a predetermined fraction of radiation incident thereupon, and a rear surface inclined at an angle to the front surface and treated with an antireflection coating to minimize reflected radiation from the rear surface, the element being selected from the family of materials consisting of semitransparent crystals and glasses wherein for near normal incidence the reflected fraction substantially equals $(n-1)^2/(n+1)^2$ where n is the index of refraction of the material at the wavelength of the incident radiation.

* * * * *